(12) United States Patent
Endo et al.

(10) Patent No.: US 10,421,261 B2
(45) Date of Patent: *Sep. 24, 2019

(54) FLAME-RETARDANT EPOXY RESIN COMPOSITION, PREPREG AND LAMINATED PLATE USING THE SAME

(71) Applicant: ADEKA CORPORATION, Tokyo (JP)

(72) Inventors: Takeshi Endo, Fukuoka (JP); Kozo Matsumoto, Fukuoka (JP); Ken-ichi Tamaso, Saitama (JP); Chihiro Asakura, Saitama (JP); Ryo Ogawa, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 12 days.

This patent is subject to a terminal disclaimer.

(21) Appl. No.: 15/547,090

(22) PCT Filed: Jan. 26, 2016

(86) PCT No.: PCT/JP2016/052160
§ 371 (c)(1),
(2) Date: Jul. 28, 2017

(87) PCT Pub. No.: WO2016/121750
PCT Pub. Date: Aug. 4, 2016

(65) Prior Publication Data
US 2018/0037014 A1   Feb. 8, 2018

(30) Foreign Application Priority Data

Jan. 29, 2015 (JP) .................................. 2015-015549

(51) Int. Cl.
| | | |
|---|---|---|
| *B32B 27/38* | (2006.01) | |
| *B32B 27/26* | (2006.01) | |
| *C08G 59/40* | (2006.01) | |
| *C08K 5/5313* | (2006.01) | |
| *C08L 63/00* | (2006.01) | |
| *C08J 5/24* | (2006.01) | |
| *C08K 5/5398* | (2006.01) | |
| *C08K 5/5399* | (2006.01) | |
| *C08K 5/00* | (2006.01) | |
| *B32B 15/092* | (2006.01) | |
| *C07F 9/32* | (2006.01) | |

(52) U.S. Cl.
CPC .............. *B32B 27/38* (2013.01); *B32B 27/26* (2013.01); *C08G 59/40* (2013.01); *C08J 5/24* (2013.01); *C08K 5/0066* (2013.01); *C08K 5/5313* (2013.01); *C08K 5/5398* (2013.01); *C08K 5/5399* (2013.01); *C08L 63/00* (2013.01); *B32B 15/092* (2013.01); *C07F 9/32* (2013.01); *C08J 2363/00* (2013.01)

(58) Field of Classification Search
CPC ......... C08L 63/00; C07F 9/32; C08K 5/0066; C08K 5/5313; C08K 5/5398; C08K 5/5399; B32B 15/092; B32B 27/38

USPC .................................................. 523/451, 452
See application file for complete search history.

(56) References Cited

U.S. PATENT DOCUMENTS

| | | |
|---|---|---|
| 3,371,046 A | 2/1968 | McCord |
| 3,383,318 A | 5/1968 | McHugh et al. |
| 3,527,850 A | 9/1970 | McHugh et al. |
| 7,524,394 B2 | 4/2009 | Nakanishi et al. |
| 2011/0245386 A1 | 10/2011 | Hill et al. |
| 2011/0319525 A1* | 12/2011 | Maeda ............... C08G 59/3218 523/452 |

(Continued)

FOREIGN PATENT DOCUMENTS

| | | |
|---|---|---|
| DE | 251134 A1COUNTRY | 11/1987 |
| EP | 3037426 A1 | 6/2016 |

(Continued)

OTHER PUBLICATIONS

International Search Report dated Mar. 15, 2016 issued in corresponding PCT/JP2016/052160 application (2 pages).
J.J. Longlet et al., "Synthesis, Structure, and Reactivity of Some N-Phosphorylphosphoranimines", Inorganic Chemistry, vol. 41. No. 24 (2002) pp. 6507-6513.
Supplementary European Search Report dated Aug. 2, 2018 issued in corresponding EP 16743353.1 (4 pages).
English Abstract of JP 2000-239491 A published Sep. 5, 2000.

*Primary Examiner* — Fred M Teskin
(74) *Attorney, Agent, or Firm* — Millen, White, Zelano and Branigan, P.C.

(57) ABSTRACT

A flame-retardant epoxy resin composition wherein (A) epoxy resin, (B) a curing agent and (C) a phosphorous-containing compound expressed by the following general formula (1) are contained; a prepreg using the same and a laminated plate using said prepreg;

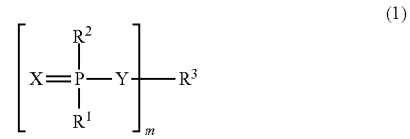

(1)

wherein m expresses an integer from 2 to 10, $R^1$ and $R^2$ each independently express an alkyl group or an aryl group, $R^3$ expresses a hydrocarbon group that may contain an oxygen atom, a sulfur atom or a nitrogen atom, X expresses an oxygen atom or a sulfur atom, Y expresses an oxygen atom, a sulfur atom or $-NR^4-$, and in this regard, $R^4$ expresses a hydrogen atom, an alkyl group or an aryl group.

6 Claims, No Drawings

(56) References Cited

U.S. PATENT DOCUMENTS

| | | | |
|---|---|---|---|
| 2012/0251810 A1* | 10/2012 | Denecke | C08J 5/24 |
| | | | 428/221 |
| 2012/0252911 A1* | 10/2012 | Fleckenstein | C08J 9/0038 |
| | | | 521/55 |
| 2014/0322541 A1* | 10/2014 | Wang | C08L 63/04 |
| | | | 428/418 |
| 2016/0152643 A1 | 6/2016 | Endo et al. | |

FOREIGN PATENT DOCUMENTS

| GB | 1121462 A | 7/1968 |
|---|---|---|
| JP | 2000-239491 A | 9/2000 |
| JP | 2012-512196 A | 5/2012 |
| SU | 584008 A | 12/1977 |
| WO | 2009/119789 A1 | 10/2009 |

* cited by examiner

FLAME-RETARDANT EPOXY RESIN COMPOSITION, PREPREG AND LAMINATED PLATE USING THE SAME

TECHNICAL FIELD

The present invention relates to a flame-retardant epoxy resin composition, and in particular relates to an environmentally-adapted flame-retardant epoxy resin composition which contains a phosphorous reactive flame retardant, and also relates to an epoxy resin laminated plate using said flame-retardant epoxy resin composition.

BACKGROUND ART

Although epoxy resin has been industrially used in a wide range of areas, more and more highly-advanced performance in epoxy resin has been required in recent years, as an industry has been developed. For example, an epoxy resin has been conventionally used for a copper-clad lamination or a material for cast molding used for electronics parts and electronics devices. From safety standpoints such as fire prevention and retardation of fire spread, a brominated epoxy resin, which brings about an effect of flame retardancy has been used for such a conventional epoxy resin. However, from the viewpoint of environmental issues, materials showing a flame-retardant effect, in place of halogen, have been actively developed in recent years.

As a prior art providing an epoxy resin with flame retardancy, a method of using a wide variety of organic phosphorus-containing compounds has been already proposed. Increasing the content rate of phosphorus in a composition is one of effective means for bringing about an effect of flame retardancy, and a method for adding a flame retardant having a high content rate of phosphorus is already known (for example, patent document 1 etc.). However, although the above method had the effect of flame retardancy to some extent, it had a disadvantage of causing a bleed phenomenon wherein a flame retardant is partially released and also a disadvantage of extremely decreasing the Tg value of a cured material in the case of curing by heating the epoxy resin composition, since the flame retardant cannot react with the epoxy resin.

In addition, a method for manufacturing a flame-retardant epoxy resin composition by using a phosphorus-containing compound, which can react with epoxy resin, is also known (For example, patent document 2 etc.). However, in the case of this method, although a problem of the aforementioned bleed phenomenon is solved by reacting the phosphorus-containing compound with the epoxy resin, there was a disadvantage in that, physical properties and thermal resistance of a cured material are decreased when the epoxy resin was cured by heating, for the reason that the phosphorus-containing compound has only one reaction point. Furthermore, there was a disadvantage as well in that workability of the phosphorus-containing compound is poor as a composition, for the reason that the phosphorus-containing compound to be used has high crystalline properties.

As a result of intensive studies for improving said disadvantages, the inventors have found a flame-retardant epoxy resin composition using a reactive phosphorus-containing compound which does not cause a bleed phenomenon of a flame retardant when cured, and physical properties of a cured material thereof does not deteriorate, and further has excellent workability, thereby achieving the present invention.

PRIOR ART DOCUMENT

Patent Document

Patent document 1: JPH09-235449 A
Patent document 2: JPH11-166035 A

SUMMARY OF THE INVENTION

Problems to be Solved by the Invention

Therefore, the first object of the present invention is to provide a flame-retardant epoxy resin composition containing an environmentally-adapted phosphorous reactive flame retardant and having excellent workability, together with excellent physical properties of a cured material thereof.

The second object of the present invention is to provide a laminated plate that has excellent environmental adaptability, and a cured material thereof has excellent physical properties as well as thermal resistance.

Means to Solve the Problems

Namely, the present invention is a flame-retardant epoxy resin composition, comprising an epoxy resin (A), a curing agent (B) and a phosphorous compound expressed by the following general formula (1) (hereafter, expressed as "phosphorus-containing compound")(C) are contained.

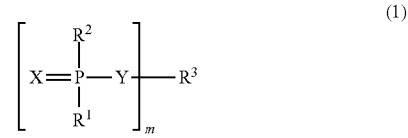

wherein m expresses an integer from 2 to 10, $R^1$ and $R^2$ each independently express an alkyl group or an aryl group, $R^3$ expresses a hydrocarbon group that may contain an oxygen atom, a sulfur atom or a nitrogen atom, X expresses an oxygen atom or a sulfur atom and Y expresses an oxygen atom, a sulfur atom or —$NR^4$—, and in this regard, $R^4$ expresses a hydrogen atom, an alkyl group or an aryl group.

Effect of the Invention

According to the present invention, although no halogen is used, a flame-retardant epoxy resin composition not only excellent in environmental adaptability and workability but also excellent in physical properties and thermal resistance of a cured material thereof can be obtained. In addition, by using said epoxy resin composition, a laminated plate excellent not only in thermal resistance and flame retardance, but also excellent in environmental adaptability can be obtained.

MODES FOR CARRYING OUT THE INVENTION

Hereinafter, an epoxy resin (A), a curing agent (B) and a phosphorus-containing compound (C) that are used in the present invention will be described.

The epoxy resin composition of the present invention is not limited in the application, particularly. For example, the epoxy resin composition of the present invention can be used for a laminated plate used for an electronic circuit card, a sealing agent, a cast molding material, a film material, an adhesive agent and an electrical insulating paint used for electronic parts, respectively, a composite material requiring flame retardancy and a powdery paint. It is preferable that the epoxy resin composition of the present invention is used especially for a laminated plate used for an electronic circuit card, a sealing agent and a cast molding material used for electronic parts, respectively, and it is most preferable that the epoxy resin composition is used for a laminated plate.

As for the epoxy resin (A) used in the present invention, it can be arbitrarily selected from any of known epoxy resins having two or more epoxy groups in a molecule, without relation to molecular structure and molecular weight etc., however, it is preferable to change these epoxy resins case by case, depending on applications for use.

Examples of said epoxy resin are, for example, bisphenol type epoxy resins such as bisphenol A type epoxy resin and bisphenol F type epoxy resin; biphenyl type epoxy resins such as biphenyl type epoxy resin and tetramethyl biphenyl type epoxy resin; dicyclopentadiene type epoxy resin; naphthalene type epoxy resin; alicyclic epoxy resin obtained from cyclohexane dimethanol and hydrogenerated bisphenol A etc.; novolac type epoxy resins such as phenolnovolac type epoxy resin, cresolnovolac type epoxy resin, bisphenol A novolac type epoxy resin, an epoxidized material that is a condensed material obtained by condensing phenols and aromatic aldehyde having a phenolic hydroxyl group, and biphenyl novolac type epoxy resin; triphenyl methane type epoxy resin; tetraphenyl ethane type epoxy resin; dicyclopentadiene-phenol addut epoxy resin; and phenol aralkyl type epoxy resin.

The aforementioned epoxy resins may be used alone or two or more kinds of them may be used together. However, in regard to the epoxy resin composition used for a laminated plate, it is preferable to use the novolac type epoxy resin and/or the bisphenol type epoxy resin.

In regard to the epoxy resin composition used for a sealing agent, it is preferable to use at least one kind of epoxy resins selected from a bisphenol type epoxy resin, a dicyclopentadiene type epoxy resin, a novolac type epoxy resin and a naphthalene type epoxy resin. In regard to the epoxy resin composition used for a cast molding material, it is preferable to use a bisphenol type epoxy resin and/or alicyclic epoxy resins.

In the case of using the epoxy resin in the present invention, a reactive diluent can be used together in order to make an adjustment to a desired viscosity. As for the reactive diluent, a reactive diluent having at least one epoxy group is used, from the viewpoint of suppressing decreases in thermal resistance and in glass-transition temperature of a cured material obtained when the epoxy resin composition is cured.

The number of epoxy group contained in said reactive diluent may be one or two or more. It is not limited in particular. Examples of the reactive diluent having one epoxy group are n-butyl glycidyl ether, glycidyl ether with alkyl group having 12 to 14 carbon atoms, allyl glycidyl ether, 2-ethylhexyl glycidyl ether, styrene oxide, phenyl glycidyl ether, cresyl glycidyl ether, p-sec-butylphenyl glycidyl ether, t-butylphenyl glycidyl ether, glycidyl methacrylate and tertiary carboxylic acid glycidyl ester.

Examples of a reactive diluent having two epoxy groups are ethylene glycol glycidyl ether, propylene glycol diglycidyl ether, butanediol diglycidyl ether, 1,6-hexanediol diglycidyl ether and neopentyl glycol diglycidyl ether. Examples of a reactive diluent having three epoxy groups are trimethylolpropane triglycidyl ether and glycerin triglycidyl ether.

The blended amount of the reactive diluent with epoxy resin is not limited in particular, however, it is preferable to vary the amount of reactive diluent used case by case, depending on different usage. In the case of an epoxy resin composition used for the laminated plate, it is preferable to use no reactive diluent from the viewpoint of avoiding a decrease in glass-transition temperature of the products. In the case of the epoxy resin composition used for the sealing agent, it is preferable to use 3 to 50 parts by mass of reactive diluent relative to 100 parts by mass of epoxy resin. 5 to 30 parts by mass of reactive diluent is even more preferable. In addition, in the case of the epoxy resin composition used for the cast molding material as well, it is preferable to use 3 to 50 parts by mass of reactive diluent relative to 100 parts by mass of epoxy resin. 5 to 30 parts by mass of reactive diluent is even more preferable.

Examples of the curing agent (B) used for the present invention are phenol resins, aliphatic amines, aromatic amines, latent curing agents and acid anhydrides. In the present invention, it is preferable to change these curing agents used case by case, depending on different usage.

Specifically, as for a usage of the laminated plate, it is preferable to use phenol resins or latent curing agents, but it is even more preferable to use a phenol novolac resin, a cresol novolac resin or a dicyan diamide type latent curing agent. As for a usage of the sealing agent, it is preferable to use a latent curing agent or acid anhydrides. As for a usage of the cast molding material, it is preferable to use aliphatic amines, aromatic amines or acid anhydrides. These curing agents may be used alone or two or more kinds of them may be used together.

Examples of the aforementioned phenol resins are polyphenol compounds such as a phenol novolac resin, a cresol novolac resin, an aromatic hydrocarbon formaldehyde resin-modified phenol resin, a dicyclopentadiene-phenol adduct resin, a phenol aralkyl resin (xylok resin), a naphthol aralkyl resin, a trisphenylol methane resin, a tetraphenylol ethane resin, a naphthol novolac resin, a naphthol-phenol co-condensed novolac resin, a naphthol-cresol co-condensed novolac resin, a biphenyl-modified phenol resin (a polyphenol compound wherein a phenol nucleus is linked with a bismethylene group), a biphenyl-modified naphthol resin (a polyvalent naphthol compound wherein a phenol nucleus is linked with a bismethylene group), an amino triazine-modified phenol resin (a compound which has a phenol skeleton, a triazine ring and a primary amino group in a molecular structure), and an alkoxy group-contained aromatic ring-modified novolac resin (a polyphenol compound wherein a phenol nucleus and an alkoxy group-contained aromatic ring are linked with formaldehyde).

The blending amount of the curing agent (B), when it is the phenol resins, with the epoxy resin (A) is not limited in particular. It is preferable, however, that there are 0.3 to 1.5 hydroxyl groups in the phenol resin relative to one epoxy group in the epoxy resin, but it is even more preferable that there are 0.8 to 1.2 hydroxyl groups in the phenol resin per one epoxy group in the epoxy resin.

Examples of the aforementioned aliphatic amines are ethylene diamine, hexamethylene diamine, 1,4-diaminocyclohexane, 1,3-diaminocyclohexane, 4,4'-diaminodicyclohexyl methane, 1,3-bis(aminomethyl)cyclohexane, 1,4-bis(aminomethyl)cyclohexane, 4,4'-diaminodicyclohexyl propane, bis(4-aminocyclohexyl) sulfone, 4,4'-diaminodicyclohexyl ether, 2,2'-dimethyl-4,4'-diaminodicyclohexane, 4,4'-diaminodicyclohexane, isophoronediamine, norbornene diamine and meta-xylene diamine. These aliphatic amines may be used alone or may be used as a mixture obtained by mixing these aliphatic amines as appropriate.

The blending amount of said curing agent (B), when it is the aliphatic amines, with the epoxy resin (A) is not limited in particular. It is preferable, however, that there are 0.6 to 1.5 active hydrogens in the aliphatic amines relative to one epoxy group in the epoxy resin, but it is even more preferable that there are 0.8 to 1.2 active hydrogens in the aliphatic amine per one epoxy group in the epoxy resin.

Examples of the aforementioned aromatic amines are diethyl toluenediamine, 1-methyl-3,5-diethyl-2,4-diaminobenzene, 1-methyl-3,5-diethyl-2,6-diaminobenzene, 1,3,5-triethyl-2,6-diaminobenzene, 3,3'-diethyl-4,4'-diaminodiphenylmethane and 3,5,3',5'-tetramethyl-4,4'-diaminodiphenyl methane. These aromatic amines may be used alone or may be used as a mixture obtained by mixing these aromatic amines in the arbitrary proportion.

The blending amount of the curing agent (B), when it is the aromatic amines, with the epoxy resin (A) is not limited in particular. It is preferable, however, that there are 0.6 to 1.5 active hydrogens in the aromatic amine relative to one epoxy group in the epoxy resin, but it is even more preferable that there are 0.8 to 1.2 active hydrogens in an aromatic amine per one epoxy group in the epoxy resin.

Examples of the aforementioned latent curing agent are latent curing agents such as a dicyandiamide type compound, an imidazole type compound and a polyamine type compound which, when mixed with epoxy resin at room temperature, do not bring a large viscosity change and physical property change to the mixture. Among these, particularly preferable curing gents are ADEKA HARDENER EH-3636AS (a dicyandiamide type latent curing agent manufactured by ADEKA CORPORATION), ADEKA HARDENER EH-4351S (The dicyandiamide type latent curing agent manufactured by ADEKA CORPORATION), ADEKA HARDENER EH-5011S (The imidazole type latent curing agent manufactured by ADEKA CORPORATION), ADEKA HARDENER EH-5046S (The imidazole type latent curing agent manufactured by ADEKA CORPORATION), ADEKA HARDENER EH-4357S (The polyamine type latent curing agent manufactured by ADEKA CORPORATION), ADEKA HARDENER EH-5057P (The polyamine type latent curing agent manufactured by ADEKA CORPORATION) and ADEKA HARDENER EH-5057PK (The polyamine type latent curing agent manufactured by ADEKA CORPORATION), which are all marketed already. These curing agents can be used alone or can be used as a mixture obtained by mixing them as appropriate.

The blending amount of said curing agent (B), selected from the aforementioned latent curing agents, with the epoxy resin (A) is not limited in particular. It is preferable, however, that there are 1 to 70 parts by mass of said curing agent (B) relative to 100 parts by mass of epoxy resin, but 3 to 60 parts by mass of the curing agent (B) relative to 100 parts by mass of the epoxy resin is even more preferable.

Examples of the aforementioned acid anhydrides are a himic anhydride, a phthalic anhydride, a maleic anhydride, a methyl himic anhydride, a succinic anhydride, a tetrahydro phthalic anhydride, a hexahydro phthalic anhydride, a methyl tetrahydro phthalic anhydride, a methyl hexahydro phthalic anhydride, a trialkyl tetrahydro phthalic anhydride-maleic anhydride addition product, a benzophenone tetracarboxylic anhydride, a trimellitic anhydride, a pyromellitic anhydride and a hydrogenated methyl nadic anhydride.

The blending amount of said curing agent (B), selected from the aforementioned acid anhydrides, with the epoxy resin (A) is not limited in particular. It is preferable, however, that there are 0.7 to 1.6 acid anhydride groups in the acid anhydride compound per one epoxy group in the epoxy resin, but it is even more preferable that there are 0.9 to 1.2 acid anhydride groups in an acid anhydride compound per one epoxy group in the epoxy resin.

In the present invention, publicly known epoxy resin curing accelerators can be used together with the aforementioned curing agent (B), if necessary. Specific examples of these curing accelerators are a phosphine compound such as triphenyl phosphine; a phosphonium salt such as tetraphenyl phosphonium bromide; imidazoles such as 2-methyl imidazole, 2-phenyl imidazole, 2-ethyl-4-methyl imidazole, 2-undecyl imidazole and 1-cyanoethyl-2-methyl imidazole; imidazole salts which are salts obtained by mixing the aforementioned imidazoles with trimellitic acid, isocyanuric acid or boronic acid; benzyl dimethylamine, amines of 2,4,6-tris(dimethylaminomethyl)phenol etc.; quarternary ammonium salts such as trimethyl ammonium chloride; and a complex compound obtained by mixing boron trifluoride with amines or ether compounds. These curing accelerators may be used alone or two or more kinds of them may be used together.

Next, a phosphorus-containing compound of the component (C) expressed by the following general formula (1), which is used in the present invention, will be described.

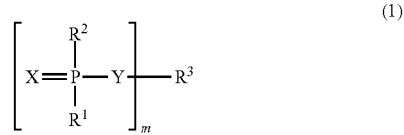

wherein m indicates an integer from 2 to 10, $R^1$ and $R^2$ indicate each independently an alkyl group or an aryl group, $R^3$ indicates a hydrocarbon group which may contain an oxygen atom, a sulfur atom or a nitrogen atom, X indicates an oxygen atom or a sulfur atom, Y indicates an oxygen atom, a sulfur atom or $-NR^4-$, and in this regard, $R^4$ indicates a hydrogen atom, an alkyl group or an aryl group.

The phosphorus-containing compound of the component (C) used in the present invention is a compound, which reacts with the epoxy group in the epoxy resin, through the reaction scheme shown in the following general formula (3)

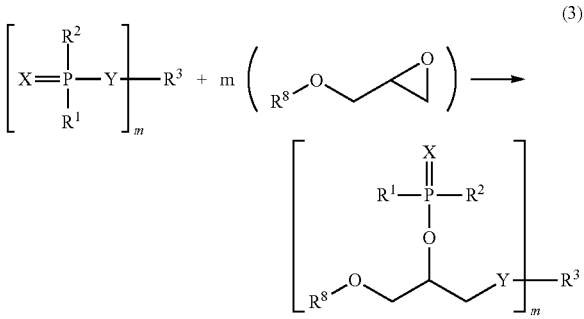

wherein m indicates an integer from 2 to 10, $R^1$ and $R^2$ indicate each independently an alkyl group or an aryl group, $R^3$ indicates a hydrocarbon group which may contain an oxygen atom, a sulfur atom or a nitrogen atom, $R^8$ indicates an alkyl group or an aryl group, X indicates an oxygen atom or a sulfur atom, Y indicates an oxygen atom, a sulfur atom or —NR$^4$—, and in this regard, R$^4$ indicates a hydrogen atom, an alkyl group or an aryl group.

In the aforementioned general formula (1), it is preferable that m is an integer from 2 to 7, but 2 to 5 is more preferable. When m is 1, only one functional group in the compound (C) can react with the epoxy group, therefore, it is not preferable since the glass-transition temperature and strength of a cured material obtained by curing the epoxy resin are markedly decreased. The case wherein m is more than 10 is not preferable for the present invention, since the manufacturing process of the phosphorus-containing compound becomes difficult for the reason that the viscosity of the composition is increased.

Examples of alkyl group expressed by R' or R$^2$ in the aforementioned general formula (1) are, for example, a methyl group, an ethyl group, a propyl group, an isopropyl group, a butyl group, an isobutyl group, a tertiary butyl group, an amyl group, an isoamyl group, a tertiary amyl group, a hexyl group, an isohexyl group, an octyl group, a 2-ethylhexyl group, a tertiary octyl group, a nonyl group and a decyl group. Also, examples of aryl group expressed by R$^1$ or R$^2$ in the aforementioned general formula (1) are, for example, a phenyl group and a naphthyl group.

In the present invention, it is preferable that R$^1$ and/or R$^2$ is an alkyl group having 1 to 6 carbon atoms among these, but an alkyl group having 2 to 5 carbon atoms is even more preferable. An ethyl group or a propyl group is optimal.

Examples of hydrocarbon group expressed by R$^3$ in the aforementioned general formula (1) are, for example, alkyl groups such as a methyl group, an ethyl group, a propyl group, an isopropyl group, a butyl group, an isobutyl group, a tertiary butyl group, an amyl group, an isoamyl group, a tertiary amyl group, a hexyl group, an isohexyl group, an octyl group, a 2-ethylhexyl group, a tertiary octyl group, a nonyl group and a decyl group; aryl groups such as a phenyl group and a naphthyl group; alkane diyl groups such as a methylene group, an ethylene group, a propylene group, an ethane diyl group and an octane diyl group; alkane triyl groups such as a methylene triyl group and a 1,1,3-ethylene triyl group; an alkane tetrayl group such as a 1,1,2,2-ethylene tetrayl group; mononuclear polyhydric phenol compounds such as hydroquinone, resorcin, pyrocatechol and phloroglucinol; and aromatic groups of polynuclear polyhydric phenol compounds such as dihydroxy naphthalene, biohenol, methylene bisphenol (bisphenol F), methylenebis (orthocresol), ethylidene bisphenol, isopropylidene bisphenol (bisphenol A), isopropylidenebis (orthocresol), tetrabromo bisphenol A, 1,3-bis(4-hydroxy cumyl benzene), 1,4-bis(4-hydroxy cumyl benzene), 1,1,3-tris(4-hydroxyphenyl)butane, 1,1,2,2-tetra(4-hydroxyphenyl)ethane, thiobisphenol, sulfonyl bisphenol, oxy bisphenol, phenol novolac, orthocresol novolac, ethylphenol novolac, butylphenol novolac, octylphenol novolac, resorcin novolac and terpene phenol.

From the viewpoint of physical properties of a cured material obtained by curing the epoxy resin composition of the present invention, it is preferable that the phosphorus-containing compound of the component (C) used in the present invention is a compound containing at least one aromatic ring in the skeleton, and it is particularly preferable that it is a compound containing groups expressed in the following general formulae from (2-1) to (2-6).

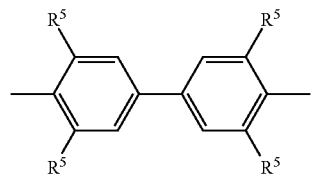

wherein R$^5$ indicates a hydrogen atom or an alkyl group having 1 to 4 carbon atoms.

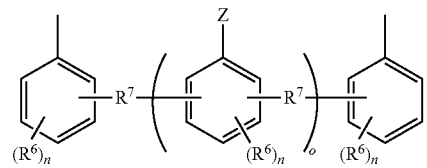

wherein n indicates an integer from 0 to 3, o indicates an integer from 0 to 50, R$^6$ indicates a hydrogen atom or an alkyl group having 1 to 4 carbon atoms, R$^7$ indicates a hydrocarbon group which may contain an oxygen atom or a sulfur atom, and Z is a hydroxyl group or a functional group expressed by the following general formula (2-3).

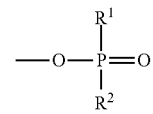

wherein R$^1$ and R$^2$ indicate each independently an alkyl group or an aryl group.

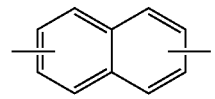

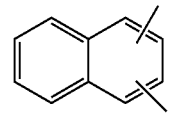

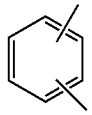

In the aforementioned general formula (1) wherein R$^3$ is a group expressed by the aforementioned general formulae from (2-1) to (2-6), it is particularly preferable to use the phosphorus-containing compound wherein the R$^3$ group has the structure expressed by the (2-1) or (2-2). In addition, in the phosphorus-containing compound wherein the R$^3$ group has the structure expressed by (2-1), the compound wherein R$^1$ and R$^2$ are each independently an ethyl group or a propyl group, and R$^5$ is a hydrogen atom or a methyl group, is particularly preferable.

On the other hand, in the case wherein the $R^3$ group has the structure of the (2-2), it is preferable that n is 0 or 1, o is an integer from 1 to 5, $R^1$ and $R^2$ are each independently an ethyl group or a propyl group, $R^6$ is a methyl group, $R^7$ is a methylene group, an ethanediyl group or a propanediyl group.

Examples of these compounds are compounds expressed by the following formulae from (4-1) to (4-4).

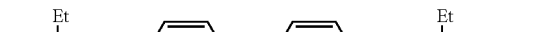
(4-1)

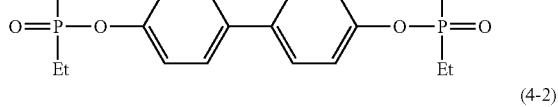
(4-2)

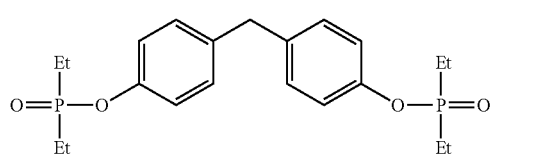
(4-3)

(4-4)

wherein p in the above formula (4-4) is an integer from 1 to 5.

The blending amount of the aforementioned phosphorus-containing compound in the epoxy resin composition of the present invention is not limited in particular, however, it is preferable that the phosphorus content contained in the aforementioned phosphorus-containing compound is 0.1 to 5 percent by mass relative to the total solid content of the epoxy resin composition, but 0.5 to 3 percent by mass is even more preferable. When the phosphorus content is less than 0.1 percent by mass, the flame retardancy of the epoxy resin composition may be markedly decreased. In contrast, when the phosphorus content is more than 5 percent by mass, the water resistance of the epoxy resin composition may be markedly decreased.

The phosphorus-containing compound used in the present invention can be manufactured by the method expressed in the following general formula (5), and the like.

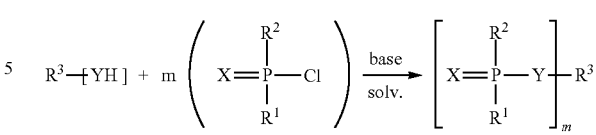
(5)

In the above formula (5), m is an integer from 2 to 10, $R^1$ and $R^2$ each independently indicate an alkyl group or an aryl group, $R^3$ indicates a hydrocarbon group which may contain an oxygen atom, a sulfur atom, or a nitrogen atom, X indicates an oxygen atom or a sulfur atom, Y indicates an oxygen atom, a sulfur atom or —$NR^4$—, and $R^4$ indicates a hydrogen atom, an alkyl group or an aryl group.

Examples of the base used in the aforementioned general formula (5) are, for example, tertiary amines such as triethylamine, tributylamine, diazabicycloundecene, diazabicyclononene and 1,4-diazabicyclo[2.2.2]octane; pyridines such as pyridine and N,N-dimethylaminopyridine; imidazoles such as 1-methylimidazole; phosphines such as triphenyl phosphine, tributyl phosphine and tricyclohexyl phosphine. In the present invention, it is preferable to use the tertiary amine among these bases, and it is most preferable to use the triethylamine.

Examples of the solvents used in the aforementioned general formula (5) are, for example, ketones such as methylethylketone, methylamylketone, diethylketone, acetone, methyl isopropylketone, propylene glycol monomethyl ether acetate and cyclohexanone; ethers such as tetrahydrofuran, 1,2-dimethoxyethane, 1,2-diethoxyethane, propylene glycol monomethyl ether; esters such as ethyl acetate and n-butyl acetate; aromatic hydrocarbons such as benzene, toluene and xylene; halogenated aliphatic hydrocarbons such as carbon tetrachloride, chloroform, trichloroethylene and methylene chloride; and halogenated aromatic hydrocarbons such as chlorobenzene. It is preferable to use ethers or halogenated aliphatic hydrocarbons among these solvents and it is particularly preferable to use ethers.

In the present invention, the aforementioned reaction can be carried out, at −80° C. to 100° C., preferably at room temperature to 50° C., for 0.5 to 72 hours, preferably 1 to 24 hours.

An organic solvent can be used as a viscosity modifier for the epoxy resin composition of the present invention, if necessary. Examples of organic solvent in this case are amides such as N,N-dimethyl formamide, ethers such as ethyleneglycol monomethylether, ketones such as acetone and methylethyl ketone, alcohols such as methanol and ethanol, and aromatic hydrocarbons etc. such as benzene and toluene. In the present invention, at least one kind of these solvents can be mixed so that the content of solvent can fall within the range from 30 to 80 percent by mass relative to the total mass of epoxy resin composition.

An inorganic filler may be added to the epoxy resin composition of the present invention, if necessary. Examples of such an inorganic filler are, for example, silica such as molten silica and crystalline silica, powders of magnesium hydroxide, aluminum hydroxide, zinc borate, zinc molybdate, calcium carbonate, silicon nitride, silicon carbide, boron nitride, calcium silicate, potassium titanate, aluminum nitride, beryllia, zirconia, zircon, forsterite, steatite, spinel, mullite and titania, or globular beads thereof, and glass fiber etc. These inorganic fillers may be used alone or two or more kinds of them may be used together, In the present invention, it is preferable to change the aforementioned inorganic fillers used case by case, depending on different usage.

As for a use application of laminated plate, it is preferable to use molten silica and aluminum hydroxide etc. As for a use application of a sealing agent, it is preferable to use molten silica and crystalline silica etc., and it is particularly preferable to use molten silica. As for a use application of a cast molding material, it is preferable to use molten silica, crystalline silica or aluminum hydroxide etc., and it is particularly preferable to use molten silica.

It is preferable that the blending amount of the aforementioned inorganic filler ranges from 20 to 90 percent by mass relative to the total solid content of the epoxy resin composition, but it is even more preferable that it ranges from 25 to 80 percent by mass. When the blending amount of the inorganic filler is less than 20 percent by mass, the effect of decreasing of coefficient of thermal expansion in a cured material tends to be decreased. When it is more than 90 percent by mass, the viscosity of epoxy resin composition is increased and workability tends to be markedly decreased.

An additive agent other than the aforementioned inorganic filler may be used together with the epoxy resin composition of the present invention, if necessary. Examples of the above additive agent are, for example, unreactive diluents (plasticizers) such as dioctyl phthalate, dibutyl phthalate, benzyl alcohol and coal tar; fibrous fillers such as glass fiber, pulp fiber, synthetic fiber and ceramic fiber; reinforcing agents such as glass cloth• aramid cloth and carbon fiber; pigment; silane coupling agents such as γ-aminopropyl triethoxysilane, N-β-(aminoethyl)-γ-aminopropyl triethoxysilane, N-β-(aminoethyl)-N'-β-(aminoethyl)-γ-aminopropyl triethoxysilane, γ-anilinopropyl triethoxysilane, γ-glycidoxypropyl triethoxysilane, β-(3,4-epoxy cyclohexyl)ethyl triethoxysilane, vinyl triethoxysilane, N-β-(N-vinylbenzylaminoethyl)-γ-aminopropyl triethoxysilane, γ-methacryloxy propyl trimethoxy silane, γ-chloropropyl trimethoxy silane and γ-mercaptopropyl trimethoxy silane; lubricants such as candelilla wax, carnauba wax, Japan wax, insect wax, bees wax, lanolin, spermaceti, montan wax, petroleum wax, fatty acid wax, fatty acid ester, fatty acid ether, aromatic ester and aromatic ether; a thickening agent; a thixotropic agent; an antioxidant; a light stabilizer; an ultraviolet absorber; a flame retardant other than the aforementioned phosphorus-containing compound; an antifoaming agent; an antirust agent; and commonly used additive agents such as colloidal silica and colloidal alumina. In the present invention, adhesive resins such as xylene resin and petroleum resin can be further used together.

The epoxy resin composition of the present invention can be used for a laminated plate used for an electronic circuit card; a sealing agent, a cast molding material, a film material, an adhesive agent and an electrical insulating paint used for electronics parts; a composite material requiring flame retardancy and a powdery paint, but in particular, it is preferable to be used for a laminated plate used for an electronic circuit card, a sealing agent and a cast molding material used for electronics parts.

The laminated plate of the present invention can be manufactured according to the following procedure: predetermined sheets of prepreg using the epoxy resin composition of the present invention, for example, 1 to 20 sheets of prepreg are overlapped, then metallic foils such as copper and aluminum are arranged on one side or on both sides thereof to laminate. After that, the thermal compression bond is carried out at a given temperature, for example, 100° C. to 250° C., by using a multiplaten press and a multiplaten vacuum press etc.

Also, the prepreg using the epoxy resin composition of the present invention can be manufactured by impregnating the epoxy resin composition of the present invention into a substrate or by applying the epoxy resin composition of the present invention to a substrate, then tack drying (B stage) the epoxy resin composition with heat etc.

The conventional materials of the substrates, for examples, inorganic fiber such as glass fiber and carbon fiber, organic fiber such as polyimide, polyester and tetrafluoroethylene, together with mixture thereof can be used for the substrate of the prepreg.

A shape of these substrates is sheet-like. Examples thereof include a woven cloth, a non-woven cloth, a roving, a chopped strand mat, and a surfacing mat. The quality of material and shape of these substrates are selected depending on use applications and performances of a molded material aimed at. If necessary, one quality of material and one shape of substrate can be used alone or two or more qualities of material and shapes of substrates can be used in combination.

The sealing agent of the present invention used for electronics parts can be manufactured by stirring, melting, mixing and dispersing the epoxy resin composition of the present invention, while heat-treating, if necessary. In this case, equipments used for stirring, melting, mixing and dispersing are not limited in particular. In the present invention, a grinder equipped with an stirring apparatus and a heating device, a triple roll mill, a ball mill, a planetary mixer, and a bead mill can be used. Also, these equipments may be used in combination as appropriate.

The cast molded material using the epoxy resin composition of the present invention can be manufactured, for example, by casting the epoxy resin composition of the present invention, obtained after mixing the epoxy resin composition with a mixer etc. and defoamed in a vacuum, into a mold.

Now, the present invention will be illustrated in greater detail by reference to the following examples and comparative examples. However, the present invention should not be construed as being limited to these examples.

In this connection, unless otherwise noted, "%" in the following examples and comparative examples is based on mass standard. And, with respect to the appearance of prepreg by visual observation, the uniform appearance was evaluated as good, and the non-uniform appearance was evaluated as poor. Similarly, with respect to the appearance of double-side copper-clad laminated plate by visual observation, which was manufactured by heat pressure curing, using a prepreg, the uniformly cured appearance was evaluated as good, and the non-uniformly cured appearance was evaluated as poor. With respect to the flame retardancy, a test piece 127 mm long by 12.7 mm wide obtained by removing the copper foil of double-side copper-clad laminated plate through the method of etch process, was tested according to "Test for Flammability of Plastic Materials UL 94" of the UL (Underwriters Laboratories) and the evaluation was made as described below.

<Evaluation Method>

A test piece was hold vertically and a burner flame came into contact with the lower end thereof for 10 seconds, then the burner flame was taken away and the length of time until the fire of the test piece went out was measured. Next, as soon as the fire went out, the second burner flame contact was carried out for 10 seconds. In the same manner as the first time, the length of time until the fire of the test piece went out was measured. In addition, at the same time, it was evaluated whether the cotton put under the test piece began to burn because of the dropping fire on it or not.

From the viewpoints of how long the test piece kept burning and whether the cotton began to burn or not in the first and second tests, the burning level was evaluated according to the UL-94V standard. V-0 of the burning level is the best. The flame retardancy becomes lower as the burning levels become V-1 and V-2 in turn. In this regard, the burning level that does not correspond to any levels from V-0 to V-2 was evaluated as NR.

The glass-transition temperature of a cured material was measured by using the TMA (EXSTAR TMA/SS-6100: a thermal mechanical analyzer manufactured by Hitachi High-Tech Science Corporation). Also, the peeling strength of copper foil was measured according to the JIS C 6481 5.7.

Manufacturing Example 1: Synthesis of a Phosphorus-containing Compound (1-1)

29.8 g (0.16 mol) of 4,4'-biphenol, 34.4 g (0.34 mol) of triethyl amine and 300 ml of super dehydrated tetrahydrofuran were introduced in a 500 ml five-necked flask equipped with an agitating blade, a reflux condenser, a thermometer, a drip funnel and a septum, which had been adequately dried and nitrogen-substituted. 47.8 g (0.34 mol) of diethyl phosphinic chloride was introduced in the drip funnel and dripping was carried out at a reaction temperature not in excess of 50° C. After finishing the dripping, stirring was carried out overnight. The reaction solution was transferred in a separating funnel and 500 ml of chloroform and 300 ml of saturated sodium bicarbonate solution were added, and the mixture was stirred well. After separating oil and water, the water layer was removed. The organic layer was washed twice with 200 ml of distilled water respectively, then was dried with anhydrous magnesium sulfate. After that, the solvent was removed with an evaporator to obtain 60.6 g (yield: 96.1%) of phosphorus-containing compound (1-1).

Manufacturing Example 2: Synthesis of a Phosphorus-containing Compound (1-2)

34.2 g (0.16 mol) of HF-1M (phenol novolac resin manufactured by Meiwa Plastic Industries, Ltd.), 34.4 g (0.34 mol) of triethyl amine and 300 ml of super dehydrated tetrahydrofuran were introduced in a 500 ml five-necked flask equipped with an agitating blade, a reflux condenser, a thermometer, a drip funnel and a septum, which had been adequately dried and nitrogen-substituted. 47.8 g (0.34 mol) of diethyl phosphinic chloride was introduced in the drip funnel and dripping was carried out at a reaction temperature not in excess of 50° C. After finishing the dripping, stirring was carried out overnight. The reaction solution was transferred in a separating funnel and 500 ml of chloroform and 300 ml of saturated sodium bicarbonate solution were added, and the mixture was stirred well. After separating oil and water, the water layer was removed. The organic layer was washed twice with 200 ml of distilled water respectively, then was dried with anhydrous magnesium sulfate. After that, the solvent was removed with an evaporator to obtain 66.4 g (yield: 98.3%) of phosphorus-containing compound (1-2).

Manufacturing Example 3: Synthesis of a Phosphorus-containing Compound (1-3)

45.7 g (0.20 mol) of bisphenol A, 42.5 g (0.42 mol) of triethyl amine and 300 ml of super dehydrated tetrahydrofuran were introduced in a 500 ml five-necked flask equipped with an agitating blade, a reflux condenser, a thermometer, a drip funnel and a septum, which had been adequately dried and nitrogen-substituted. 59.0 g (0.42 mol) of diethyl phosphinic chloride was introduced in the drip funnel and dripping was carried out at a reaction temperature not in excess of 50° C. After finishing the dripping, stirring was carried out overnight. The reaction solution was transferred in a separating funnel and 500 ml of chloroform and 300 ml of saturated sodium bicarbonate solution were added, and the mixture was stirred well. After separating oil and water, the water layer was removed. The organic layer was washed twice with 200 ml of distilled water respectively, then was dried with anhydrous magnesium sulfate. After that, the solvent was removed with an evaporator to obtain 78.1 g (yield: 89.4%) of phosphorus-containing compound (1-3).

Manufacturing Example 4: Synthesis of a Phosphorus-containing Compound (1-4)

32.0 g (0.16 mol) of bisphenol F, 34.4 g (0.34 mol) of triethyl amine and 300 ml of super dehydrated tetrahydrofuran were introduced in a 500 ml five-necked flask equipped with an agitating blade, a reflux condenser, a thermometer, a drip funnel and a septum, which had been adequately dried and nitrogen-substituted. 47.8 g (0.34 mol) of diethyl phosphinic chloride was introduced in the drip funnel and dripping was carried out at a reaction temperature not in excess of 50° C. After finishing the dripping, stirring was carried out overnight. The reaction solution was transferred in a separating funnel and 500 ml of chloroform and 300 ml of saturated sodium bicarbonate solution were added, then the mixture was stirred well. After separating oil and water, the water layer was removed. The organic layer was washed twice with 200 ml of distilled water respectively, then was dried with anhydrous magnesium sulfate. After that, the solvent was removed with an evaporator to obtain 60.9 g (yield: 93.2%) of phosphorus-containing compound (1-4).

Example 1

49.1 g of EOCN-104 S (cresol novolac type epoxy resin manufactured by NIPPON KAYAKU Co., Ltd), 60.1 g of HP-350 (aluminum hydroxide manufactured by SHOWA DENKO K.K.) and 60.1 g of SFP-130MC (spherical silica manufactured by DENKI KAGAKU KOGYO KABUSHIKI KAISHA) were added to 100 g of methyl ethyl ketone and the mixture were dispersed with a triple roll mill. Next, 15.3 g of phosphorus-containing compound (1-1) obtained in Manufacturing example 1 which was dissolved in 3 g of methanol, was added. Furthermore, 50.9 g of EOCN-104S, 5 g (5 phr) of ADEKA HARDENER EH-3636AS (a dicyandiamide type latent curing agent manufactured by ADEKA CORPORATION), and 100 g of methyl ethyl ketone were added, and the obtained mixture was dispersed with a disperser to manufacture resin varnish.

The obtained resin varnish was impregnated in glass cloth (#7628 manufactured by Nitto Boseki Co., Ltd.) and was dried by heating in a circulating hot air oven at 120° C. for 10 minutes to manufacture a prepreg. The amount of resin in the obtained prepreg was 40 to 50 percent by mass of the whole prepreg. Then, four sheets of prepreg manufactured were overlapped entirely and copper foils 35 μm thick (manufactured by FUKUDA METAL FOIL & POWDER Co., LTD.) were arranged on both outsides of the overlapped prepregs. Then the thermal compression was carried out under a condition of 190° C. and 10 Kg/cm² for 120 minutes to obtain a both sides copper-clad laminated plate. Physical properties of the both sides copper-clad laminated plate manufactured as above were shown in Table 1.

Manufacturing Example 5: Synthesis of a Phosphorus-containing Compound (1-5)

28.2 g (0.30 mol) of phenol, 32.4 g (0.32 mol) of triethyl amine and 300 ml of super dehydrated tetrahydrofuran were introduced in a 500 ml four-necked flask equipped with a rotator, a reflux condenser, a drip funnel and a septum, which had been adequately dried and nitrogen-substituted. 45.0 g (0.32 mol) of diethyl phosphinic chloride was introduced in the drip funnel and dripping was carried out at a reaction temperature not in excess of 50° C. After finishing the dripping, stirring was carried out overnight. The reaction solution was transferred to a separating funnel and 500 ml of chloroform and 300 ml of saturated sodium bicarbonate solution were added, then the mixture was stirred well. After separating oil and water, the water layer was removed. The organic layer was washed twice with 200 ml of distilled water respectively, then was dried with anhydrous magnesium sulfate. After that, the solvent was removed with an evaporator to obtain 50.7 g (yield: 85.3%) of phosphorus-containing compound (1-5).

Examples from 2 to 4 and Comparative Examples from 1 to 4

The both sides copper-clad laminated plate was manufactured in the same way as Example 1, except that the blending was carried out according to the composition described in Table 1 and various evaluations were made. Results were shown in Table 1.

TABLE 1

| | Exam. 1 | Exam. 2 | Exam. 3 | Exam. 4 | Comp. Exam. 1 | Comp. Exam. 2 | Comp. Exam. 3 | Comp. Exam. 4 |
|---|---|---|---|---|---|---|---|---|
| EOCN-104S | 100 | 100 | 100 | 100 | 100 | 100 | 100 | 100 |
| EH-3636AS | 5 | 5 | 5 | 5 | 5 | 5 | 5 | 5 |
| Phosphorus-containing compound (1-1) | 15.3 | | | | | | | |
| Phosphorus-containing compound (1-2) | | 16.6 | | | | | | |
| Phosphorus-containing compound (1-3) | | | 7.70 | 17.2 | | | | |
| Phosphorus-containing compound (1-5) | | | | | | | | 15.4 |
| HCA-HQ[*1] | | | | | | 27.5 | | |
| FP-600[*2] | | | | | | | 30.4 | |
| HP-350 | 60.1 | 60.8 | 53.9 | 61.1 | 65.7 | 67.7 | 52.5 | 60.2 |
| SFP-130MC | 60.1 | 60.8 | 53.9 | 61.1 | 65.7 | 67.7 | 52.5 | 60.2 |
| Appearance of prepreg | Good | Good | Good | Good | Poor | Good | Good | Good |
| Appearance of laminated plate | Good | Good | Good | Good | — | Poor | Good | Good |
| Tg(° C.) | 181 | 177 | 175 | 172 | — | 166 | 178 | 175 |
| Flame retardancy (UL-94) | V-0 | V-0 | V-1 | V-1 | — | V-0 | NR | NR |
| Peeling strength of copper foil | 1.33 | 1.33 | 1.24 | 1.24 | — | 1.30 | 1.38 | 1.30 |

[*1]HCA-HQ: a compound expressed by the following structural formula (6), manufactured by SANKO Company, Limited

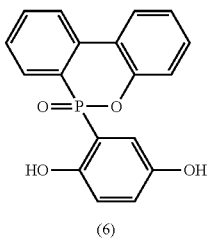

(6)

*2FP-600: a compound expressed by the following structural formula (7), manufactured by ADEKA CORPORATION

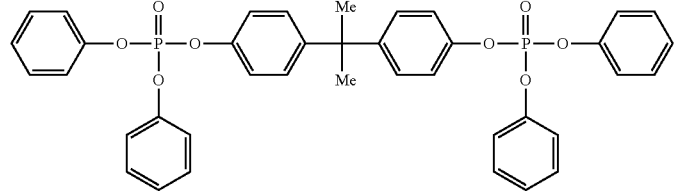

(7)

In the comparative example 1, a uniform prepreg could not be obtained, for the reason that the phosphorus-containing compound used was crystallized when the prepreg was manufactured, therefore, subsequent evaluations could not be made. In the comparative example 2, a uniform laminated plate could not be obtained, for the reason that a component which seems to be FP-600 is partially separated in pressure curing when the both sides copper-clad laminated plate was manufactured.

From the results in Table 1, it was confirmed that the laminated plate using the flame-retardant epoxy resin composition of the present invention shows excellent flame retardant properties.

INDUSTRIAL APPLICABILITY

The flame-retardant epoxy resin composition of the present invention has excellent environmental adaptability due to nonuse of halogen, furthermore, has not only excellent workability but also advantages in that a bleed phenomenon of flame retardant, when cured, does not occur and physical properties of cured material are not decreased due to use of a phosphorous flame retardant having two or more reaction points which can react with an epoxy group of epoxy resin. Especially, a laminated plate etc. manufactured by using the flame-retardant epoxy resin composition of the present invention have not only excellent flame retardancy, but also excellent manufacturing adaptability, environmental adaptability and physical properties. Therefore, the present invention is extremely useful in the industrial field.

The invention claimed is:

1. A flame-retardant epoxy resin composition comprising (A) epoxy resin, (B) a curing agent and (C) a phosphorous-containing compound expressed by formula (1);

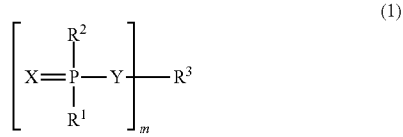

(1)

wherein m expresses an integer from 2 to 10, $R^1$ and $R^2$ each independently express an alkyl group or an aryl group, $R^3$ expresses a hydrocarbon group that may contain an oxygen atom, a sulfur atom or a nitrogen atom, X expresses an oxygen atom or a sulfur atom, Y expresses an oxygen atom, a sulfur atom or —$NR^4$—, and in this regard, $R^4$ expresses a hydrogen atom, an alkyl group or an aryl group.

2. The epoxy resin composition according to claim 1, wherein $R^3$ in formula (1) is a hydrocarbon group having at least one aromatic ring.

3. The epoxy resin composition according to claim 1, wherein X and Y in formula (1) are both oxygen atoms, $R^1$ and $R^2$ are each independently an alkyl group having 1 to 4 carbon atoms, and $R^3$ is a group having any one of structures of formula (2-1), (2-2), (2-4), (2-5), or (2-6):

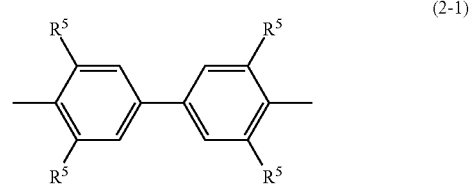

(2-1)

wherein $R^5$ indicates a hydrogen atom or an alkyl group having 1 to 4 carbon atoms;

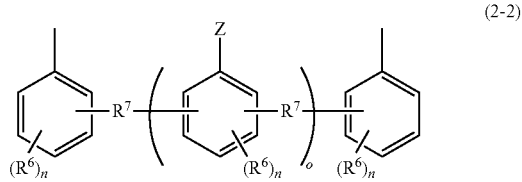

(2-2)

wherein n indicates an integer from 0 to 3, o indicates an integer from 0 to 50, $R^6$ indicates a hydrogen atom or an alkyl group having 1 to 4 carbon atoms, $R^7$ indicates a hydrocarbon group which may contain an oxygen atom or a sulfur atom, and Z is a hydroxyl group or a functional group expressed by formula (2-3);

(2-3)

wherein $R^1$ and $R^2$ each independently indicate an alkyl group or an aryl group;

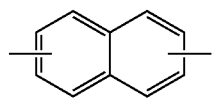 (2-4)

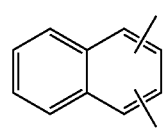 (2-5)

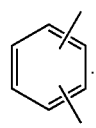 (2-6)

4. A prepreg comprising a sheet-like substrate material made of at least one inorganic fiber or organic fiber, and the epoxy resin composition according to claim 1.

5. A method for manufacturing an epoxy resin laminated plate wherein metallic foils are arranged on at least one surface of the prepreg described in claim 4 or at least one surface of a laminated body, which is prepared by overlapping two or more sheets of the prepreg, by thermal compression treatment to obtain the laminated plate.

6. An epoxy resin laminated plate manufactured by the method according to claim 5.

\* \* \* \* \*